United States Patent [19]

Sirrenberg et al.

[11] 4,277,499
[45] Jul. 7, 1981

[54] COMBATING INSECTS WITH N-(SUBSTITUTED-PHENYL)-N-(2-CHLORO-6-FLUORO-BENZOYL)-UREAS

[75] Inventors: Wilhelm Sirrenberg, Sprockhoevel; Erich Klauke, Odenthal; Albrecht Marhold, Leverkusen; Ingeborg Hammann, Cologne; Wilhelm Stendel, Wuppertal; Ingomar Krehan, Cologne, all of Fed. Rep. of Germany

[73] Assignee: Bayer Aktiengesellschaft, Leverkusen, Fed. Rep. of Germany

[21] Appl. No.: 117,755

[22] Filed: Feb. 1, 1980

Related U.S. Application Data

[63] Continuation of Ser. No. 971,777, Dec. 21, 1978, abandoned.

[30] Foreign Application Priority Data

Jan. 13, 1978 [DE] Fed. Rep. of Germany ....... 2801316

[51] Int. Cl.³ .................... C07C 127/22; A01N 9/20
[52] U.S. Cl. ........................................ 424/322; 564/44
[58] Field of Search ................. 260/553 E; 424/322; 564/44

[56] References Cited

U.S. PATENT DOCUMENTS

| 4,013,717 | 3/1977 | Wellinger et al. ........... 260/553 E |
| 4,085,226 | 4/1978 | Sirrenberg et al. ......... 260/553 E X |
| 4,089,975 | 5/1978 | Wade et al. .................. 260/553 E X |
| 4,139,636 | 6/1979 | Sirrenberg et al. ............ 424/322 |
| 4,170,657 | 10/1979 | Rigterink ....................... 424/322 |

FOREIGN PATENT DOCUMENTS 2601780  7/1977  Fed. Rep. of Germany ....... 260/553 E

OTHER PUBLICATIONS

Wellinga et al., J. Agr. Food Chem., vol. 21, No. 6 (1973), pp. 993–998.

*Primary Examiner*—Thomas A. Waltz
*Attorney, Agent, or Firm*—Sprung, Felfe, Horn, Lynch & Kramer

[57] ABSTRACT

N-(Substituted-phenyl)-N'-(2-chloro-6-fluoro-benzoyl)-ureas of the formula

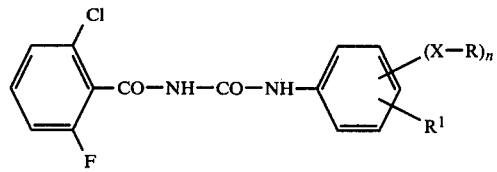

in which
R represents halogenoalkyl with 1–4 carbon atoms,
$R^1$ represents hydrogen, halogen or halogenoalkyl with 1–4 carbon atoms,
X represents oxygen or sulphur, and
n represents the number 1 or 2 which possess insecticidal properties.

6 Claims, No Drawings

COMBATING INSECTS WITH N-(SUBSTITUTED-PHENYL)-N-(2-CHLORO-6-FLUORO-BENZOYL)-UREAS

This is a continuation of application Ser. No. 971,777, filed Dec. 21, 1978, now abandoned.

The present invention relates to and has for its objects the provision of particular new N-phenyl-N'-(2-chloro-6-fluoro-benzoyl)-urea compounds, processes for their preparation and their use as insecticides, which possess insecticidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is already known that certain benzoylureas, such as N-(2,6-difluorobenzoyl)-N'-(4-chlorophenyl)-urea, possess insecticidal properties (see J. Agr. Food Chem., volume 21 No. 6 (1973), page 993-8).

The present invention provides, as new compounds, the N-phenyl-N'-(2-chloro-6-fluoro-benzoyl)-ureas of the general formula

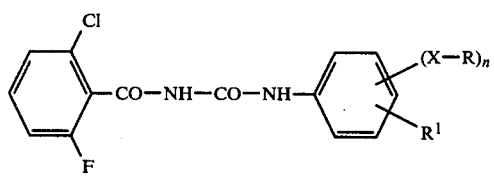

in which
R represents halogenoalkyl with 1 to 4 carbon atoms,
$R^1$ represents hydrogen, halogen or halogenoalkyl,
X represents oxygen or sulphur, and
n represents the number of 1 or 2.

Preferably, R represents straight-chain or branched halogenoalkyl with 1 to 4 (especially 1 or 2) carbon atoms and 1 to 4 halogen atoms and $R^1$ represents hydrogen, chlorine or trifluoromethyl.

Surprisingly, the new N-phenyl-N'-(2-chloro-6-fluoro-benzoyl)-ureas according to the invention exhibit a considerably better insecticidal action than the very closely related compounds of analogous structure and the same type of action which are already known from the state of the art. The products according to the present invention thus represent a true enrichment of the art.

The invention also provides a process for the preparation of an N-phenyl-N'-(2-chloro-6-fluoro-benzoyl)-urea of the formula (I) in which
(a) a substituted aniline of the general formula

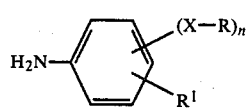

in which
R, $R^1$, X and n have the meanings stated above, is reacted with 2-chloro-6-fluoro-benzoyl isocyanate, optionally in the presence of a diluent, or (b) a substituted phenyl isocyanate of the general formula

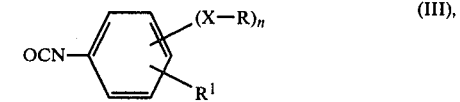

in which
R, $R^1$, X and n have the meanings stated above, is reacted with 2-chloro-6-fluoro-benzamide, optionally in the presence of a diluent.

If, according to process variant (a), 3-chloro-4-trifluoromethoxy-aniline and 2-chloro-6-fluoro-benzoyl isocyanate are used as starting materials, and according to process variant (b), 3-chloro-4-trifluoromethoxy-phenyl isocyanate and 2-chloro-6-fluoro-benzamide are used as starting materials, the course of the reactions can be represented by the equations which follow:

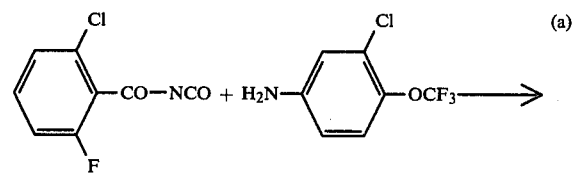

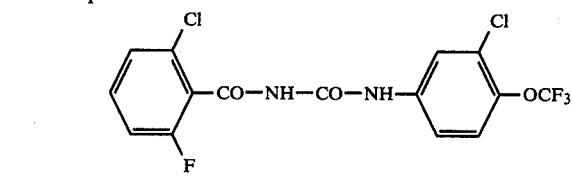

The following compounds of the formula (I) may be mentioned in particular: N-[2-chloro-5-(2-chloro-1,1,2-trifluoroethoxy)]-phenyl-, N-[4-chloro-3-(2-chloro-1,1,2-trifluoroethoxy)]-phenyl-, N-[3-(2-chloro-1,1,2-trifluoroethoxy)]-phenyl-, N-[3-chloro-4-(chlorodifluoromethoxy)]-phenyl-, N-[3-chloro-4-(chlorodifluoromethylthio)]-phenyl-, N-[2-chloro-4-(chlorodifluoromethoxy)]-phenyl-, N-[2-chloro-4-(chlorodifluoromethylthio)]-phenyl-, N-[2-chloro-5-(chlorodifluoromethoxy)]-phenyl- and N-[2-chloro-5-(trifluoromethylthio)]-phenyl-N'-(2-chloro-6-fluorobenzoyl)-urea.

Substituted anilines of the formula (II) to be used as starting materials are known and can be prepared by processes which are known from the literature [see, for example, J. Org. Chem. 25 (1960), 965 and 29 (1964), 1; J. Am. Chem. Soc. 73 (1951) 5,831; Bull. Soc. Chim. France 4 (1957), 531; Z. obsc. Chim. 35 (1965), 1,377 English Translation; J. Am. Chem. Soc. 83 (1961), 4,360 and U.S. Pat. No. 3,387,037]; the amino group can be converted into the isocyanate group by customary processes, for example by reaction with phosgene, by which means the corresponding isocyanates of the formula (III) are obtained.

Examples of the compounds (II) and (III) which may be mentioned are: 4-difluoromethoxy-, 4-difluoromethylthio, 3-difluoromethoxy-, 3-difluoromethylthio, 2-difluoromethoxy-, 2-difluoromethylthio-, 4-trifluoromethoxy-, 4-trifluoromethylthio-, 3-trifluoromethoxy-, 3-trifluoromethylthio-, 2-trifluoromethoxy-, 2-trifluoromethylthio-, 4-chlorodifluoromethoxy-, 4-chlorodifluoromethylthio-, 3-chlorodifluoromethoxy-, 3-chlorodifluoromethylthio-, 2-chlorodifluoromethoxy-, 2-chlorodifluoromethylthio-, 3-trifluoromethyl-4-trifluoromethoxy-, 3-trifluoromethyl-4-trifluoromethylthio-, 3-trifluoromethyl-4-difluoromethoxy-, 3-trifluoromethyl-4-trifluoromethylthio-, 3,4-bis-(difluoromethoxy)-, 3,4-bis-(difluoromethylthio)-, 3,4-bis-(trifluoromethoxy)-, 3,4-cis-(trifluoromethylthio)-, 2-chloro-4-trifluoromethoxy-, 2-chloro-4-trifluoromethylthio-, 3-chloro-4-trifluoromethoxy-, 3-chloro-4-trifluoromethylthio-, 2-chloro-4-chlorodifluoromethoxy-, 2-chloro-4-chlorodifluoromethylthio, 3-chloro-4-chlorodifluoromethoxy-, 3-chloro-4-chlorodifluoromethyl-, thio-, 2-(1,1,2,2-tetrafluoroethoxy)-, 3-(1,1,2,2-tetrafluoroethoxy)-, 4-(1,1,2,2-tetrafluoroethoxy)-, 2-chloro-4-(1,1,2,2-tetrafluoroethoxy)-, 3-chloro-4-(1,1,2,2-tetrafluoroethoxy)-, 4-(2-chloro-1,1,2-trifluoroethoxy)-, 2-chloro-4-(2-chloro-1,1,2,-trifluoroethoxy)-, 3-chloro-4-(2-chloro-1,1,2-trifluoroethoxy)- and 4-(2-chloro-1,1,2-trifluoroethylthio)-aniline or -phenyl isocyanate.

2-Chloro-6-fluoro-benzoyl isocyanate and 2-chloro-6-fluorobenzamide, also used as starting materials for the synthesis process according to the invention, can be prepared by methods which are known from the literature [see J. Org. Chem. 30 (1965), 4,306 and Beilstein "Handbuch der organischen Chemie" ("Handbook of organic Chemistry") volume 9, page 336].

The process variants for the preparation of the N-phenyl-N'-benzoyl-ureas according to the invention are preferably carried out using suitable diluents. Possible diluents are virtually all the inert organic solvents, especially aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl, ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

The reaction temperature in either process variant can be varied within a substantial range. In general, the reaction is carried out at from 0° and 120° C., preferably at from 70° to 85° C.

In general, the reaction is allowed to proceed under normal pressure.

For carrying out either process variant, the starting components are preferably employed in equimolar amounts. An excess of one or other of the reactants brings no substantial advantages.

In general, the reactants are brought together in one of the solvents indicated. The phenyl isocyanates (III) to be employed in reaction variant (b) can be employed in the pure form or, without isolation, in the form of their reaction mixture, which is obtained after reacting the corresponding aniline with phosgene. To this reaction mixture, preferably in one of the solvents indicated above, is added 2-chloro-6-fluoro-benzamide.

The reactions are carried out under the conditions indicated above and the products are isolated by filtration. The new compounds are obtained in the crystalline form, with a sharp melting point.

As already mentioned, the N-phenyl-N'-(2-chloro-6-fluoro-benzoyl)-ureas according to the invention are distinguished by an excellent insecticidal activity. They are active, in the veterinary medicine field, against animal parasites (ectoparasites), such as parasitic fly larvae. When used in "feed theory" applications, they control manure-breeding insects, which are known to be vector in the transmission of various animal diseases.

The active compounds are well tolerated by plants, have a favorable level of toxicity to warm-blooded animals, and can be used for combating arthropod pests, especially insects and arachnids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria,*

*Euproctis chrysorrhoea*, Lymantria spp., *Bucculatrix thurberiella, Phyllocnistis citrella*, Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol esters, for example alkylaryl polyglycol ethers, alkyl sulphonates, alkyl sulphates, aryl sulphonates as well as aloumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods, especially insects, which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects by the application to said animals of a compound according to the present invention, in admixture with a diluent or carrier.

The preparation of the novel compounds is shown in the following illustrative examples:

EXAMPLE 1

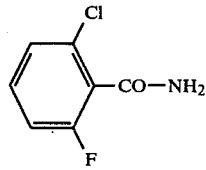

2-chloro-6-fluoro-benzamide was prepared from 2-chloro-6-fluoro-benzoic acid chloride and ammonia by processes known from the literature. It had a melting point of 138° C.

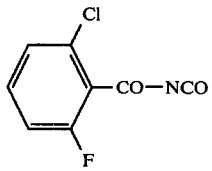

2-chloro-6-fluoro-benzoyl isocyanate was prepared by the process known from the literature (see Speziale et al., J. Org. Chem. 30 (12) page 4, 306-7 (1965). It had a boiling point of 75° C./1 mm Hg.

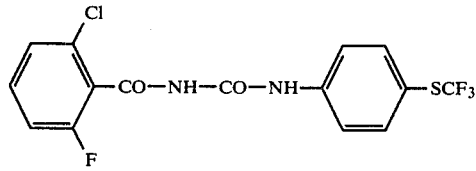

(1)

3.87 g (0.02 mol) of 4-trifluoromethylmercaptoaniline were dissolved in 50 ml of dry toluene. A solution of 3.99 g (0.02 mol) of 2-chloro-6-fluoro-benzoyl isocyanate in 15 ml of toluene was added to this solution at 60° C. The mixture was stirred at 80° C. for 1 hour and then cooled to room temperature. After drying, 5.4 g (69% of theory) of N-(4-trifluoromethylmercaptophenyl)-N-(2-chloro-6-fluoro-benzoyl)-urea were obtained. The product had a melting point of 202° C.

The compounds in the following table were also prepared by an analogous procedure, optimization of the yields not having been effected, but being possible. The purity and identity of the products were established by elementary analysis and NMR spectra.

TABLE 1

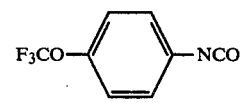

(I)

| Compound No. | R | $R^1$ | n | x | Melting point (°C.) | Yield (% of theory) |
|---|---|---|---|---|---|---|
| 2 | 4-$CF_3$ | H | 1 | O | 180 | 63.5 |
| 3 | 3-$CF_3$ | H | 1 | O | 162 | 67.5 |
| 4 | 2-$CF_3$ | H | 1 | O | 154 | 67.5 |
| 5 | 4-$CF_3$ | 3-Cl | 1 | O | 189 | 74 |
| 6 | 4-$CF_3$ | 2-Cl | 1 | O | 221 | 95.5 |
| 7 | 4-$CHF_2$ | H | 1 | O | 173-4 | 83.5 |
| 8 | 3-$CHF_2$ | H | 1 | O | 132 | 72.5 |
| 9 | 3,4-$CHF_2$ | H | 2 | O | 195 | 89 |
| 10 | 4-$CHF_2$ | 3-$CF_3$ | 1 | O | 221 | 84.5 |
| 11 | 4-$CF_2Cl$ | H | 1 | O | 203 | 82.5 |
| 12 | 4-$CF_2$-CHFCl | H | 1 | O | 199 | 83.5 |
| 13 | 4-$CF_2$-CHFCl | 3-Cl | 1 | O | 178 | 70.5 |
| 14 | 4-$CF_2$-$CHF_2$ | 3-Cl | 1 | O | 176 | 90.0 |
| 15 | 3-$CF_2$-$CHF_2$ | H | 1 | O | 185 | 69.5 |
| 16 | 3-$CF_3$ | H | 1 | S | 172 | 43 |
| 17 | 4-$CF_3$ | 3-Cl | 1 | S | 187 | 54 |
| 18 | 4-$CF_2Cl$ | 3-Cl | 1 | S | 176 | 60.5 |
| 19 | 4-$CF_2$CHFCl | H | 1 | S | 189 | 91.5 |

The compounds according to the invention could also be prepared by reacting 2-chloro-6-fluoro-benzamide with the corresponding isocyanates.

EXAMPLE 2

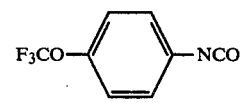

4-Trifluoromethoxy-phenyl isocyanate was prepared (with a boiling of 37° C./1 mm Hg and a refractive index $n_D^{20}$ of 1.4600) from the corresponding aniline and phosgene by the process known from the literature.

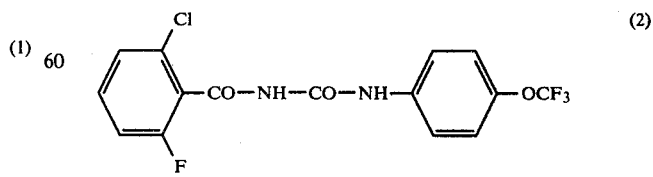

(2)

5.02 g (0.03 mol) of 2-chloro-6-fluoro-benzamide were suspended in 50 ml of dry toluene. A solution of 6.1 g (0.03 mol) of 4-trifluoromethoxy-phenyl isocyanate in 10 ml of toluene was added to this suspension and the mixture was boiled under reflux for 5 hours. Thereafter, the mixture was cooled to room temperature and the product which had precipitated was filtered off. It was recrystallized from toluene and had a melting point of 178° C. The purity and identity were established by elementary analysis and NMR spectrum. The NMR spectrum was identical to the spectrum of the substance prepared by the other route.

The insecticidal activity of the compounds of this invention is illustrated by the following examples wherein the compounds according to the present invention are each identified by the number (given in brackets) from the preparative examples hereinabove.

EXAMPLE 3

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined. In this test compounds (1), (2), (5), (11), (12), (13), (17) and (18) showed a superior activity compared to the prior art.

EXAMPLE 4

Mosquito larvae test

Test insects: Aedes aegypti larvae
Solvent: 99 parts by weight of acetone
Emulsifier: 1 part by weight of alkylaryl polyglycol ether To produce a suitable preparation, the active compound was dissolved, at a rate of 2 g per liter, in the solvent containing the amount of emulsifier stated above. The solution thus obtained was diluted with water to the desired lower concentrations.

The aqueous preparations of the active compound were placed in glass vessels and about 25 mosquito larvae were then placed in each glass vessel.

After 24 hours, the degree of destruction was determined. In this test compounds (1), (12) and (17) showed a superior action compared to the prior art.

EXAMPLE 5

Test with parasitic fly larvae

Solvent: 80 parts by weight of alkylaryl polyglycol ether

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined. In this test compounds (1), (12) and (17) showed superior action compared to the prior art.

It will be appreciated that the instant specification and examples are set forth by way of illustration and not limitation and that various modifications and changes may be made without departing from the spirit and scope of the present invention.

What is claimed is:

1. An N-(substituted-phenyl)-N'-(2-chloro-6-fluorobenzoyl)-urea selected from the group consisting of
   N-(4-trifluoromethylmercaptophenyl)-N'-(2-chloro-6-fluoro-benzoyl)-urea,
   N-(4-trifluoromethoxyphenyl)-N'-(2-chloro-6-fluoro-benozyl)-urea, and
   N-[3-chloro-4-(trifluoromethylmercapto)]-phenyl-N'-(2-chloro-6-fluoro-benzoyl)-urea.

2. A compound according to claim 1, wherein such compound is N-(4-trifluoromethylmercaptophenyl)-N'-(2-chloro-6-fluoro-benzoyl)-urea of the formula

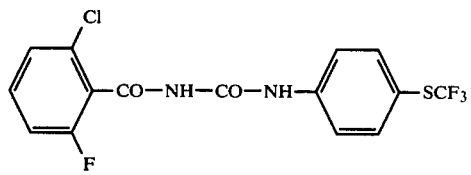

3. A compound according to claim 1, wherein such compound is N-(4-trifluoromethoxyphenyl)-N'-(2-chloro-6-fluoro-benzoyl)-urea of the formula

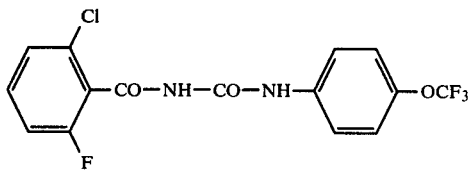

4. A compound according to claim 1, wherein such compound is N-[3-chloro-4-(trifluoromethylmercapto)]-phenyl-N'-(2-chloro-6-fluoro-benzoyl)-urea of the formula

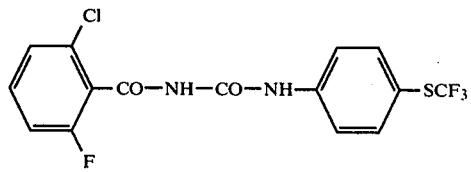

5. An insecticidal composition containing as active ingredient an insecticidally effective amount of a compound according to claim 1 in admixture with a diluent.

6. A method of combating insects which comprises applying to the insects, or to a habitat thereof, an insecticidally effective amount of a compound according to claim 1.

UNITED STATES PATENT AND TRADEMARK OFFICE
CERTIFICATE OF CORRECTION

PATENT NO. : 4,277,499
DATED : July 7, 1981
INVENTOR(S) : Wilhelm Sirrenberg, et al It is certified that error appears in the above—identified patent and that said Letters Patent is hereby corrected as shown below:

Column 6, line 25 "aloumin" should read "albumin"

Column 8, line 47 "a)" was omitted

Column 8, line 57 "b)" was omitted

Column10, lines 45 to 57 cancel and substitute with

-- 4. A compound according to claim 1, wherein such compound is N-[3-chloro-4-(trifluoromethylmercapto)]-phenyl-N'-(2-chloro-6-fluoro-benzoyl)-urea of the formula

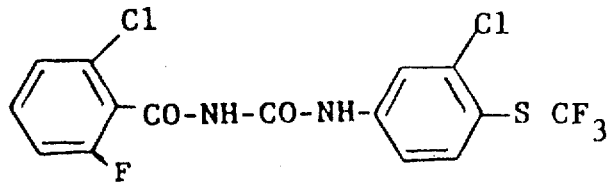

--.

Signed and Sealed this

Twenty-ninth Day of September 1981

[SEAL]

Attest:

GERALD J. MOSSINGHOFF

Attesting Officer    Commissioner of Patents and Trademarks